United States Patent [19]

Prabhudass

[11] Patent Number: 4,875,496
[45] Date of Patent: Oct. 24, 1989

[54] ORAL HYGIENE TOOL

[76] Inventor: Israel Prabhudass, Box 1173, Fort St. James, B.C., Canada, V0J 1P0

[21] Appl. No.: 213,635

[22] Filed: Jun. 30, 1988

[51] Int. Cl.⁴ .......................................... A61C 15/00
[52] U.S. Cl. .................................................. 132/329
[58] Field of Search ........................ 132/321, 328, 329; 433/141

[56] References Cited

U.S. PATENT DOCUMENTS

| D. 32,481 | 4/1900 | Berger | D24/23 |
|---|---|---|---|
| D. 44,390 | 7/1913 | Weder | D24/30 |
| D. 159,920 | 8/1950 | Pavlinetz | D7/137 |
| D. 161,947 | 2/1951 | Margolis | D7/137 |
| D. 215,775 | 10/1969 | Jones | D24/23 |
| D. 249,802 | 10/1978 | Lyman | D24/23 |
| 682,892 | 9/1901 | Thurston | 132/328 |
| 1,451,380 | 4/1923 | Thum | 132/329 |
| 4,271,854 | 9/1981 | Bengtsson | 132/329 |

Primary Examiner—Robert Peshock
Attorney, Agent, or Firm—Leon Gilden

[57] ABSTRACT

An oral hygiene tool is set forth formed of a resilient one-piece flexible material of a relatively thin, rectangular cross-sectional configuration. The tool includes a relatively wide centrally disposed tongue-scraping blade and a pair of handles extending from either end of said blade and integrally formed thereto. The tool is configured and arranged for telescoping acceptance within an associated toothbrush handle and may be formed with a widened tip at either terminal end of each handle for alignment within a cavity defined within said handle at one end and providing a grasping tip at the other end that depends outwardly of said handle.

1 Claim, 2 Drawing Sheets

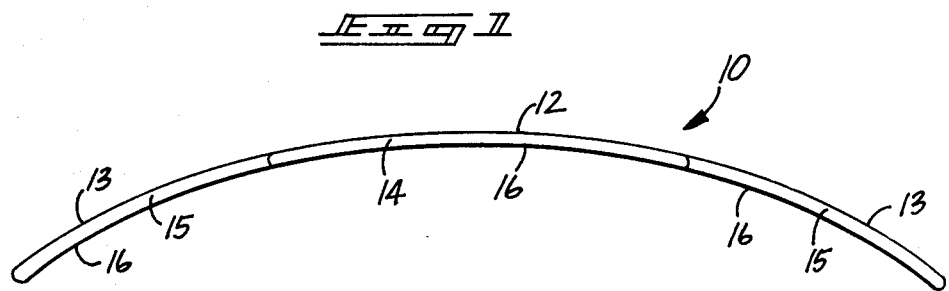
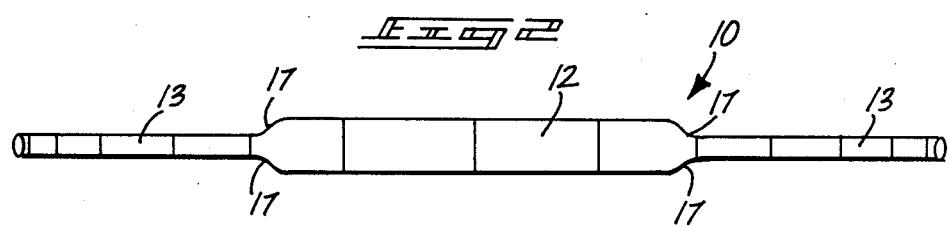
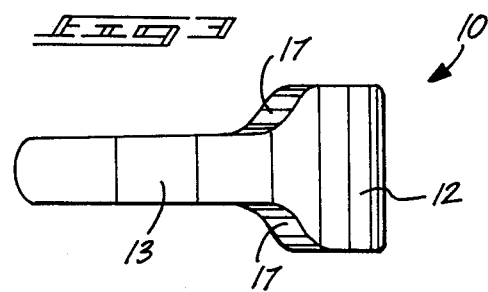

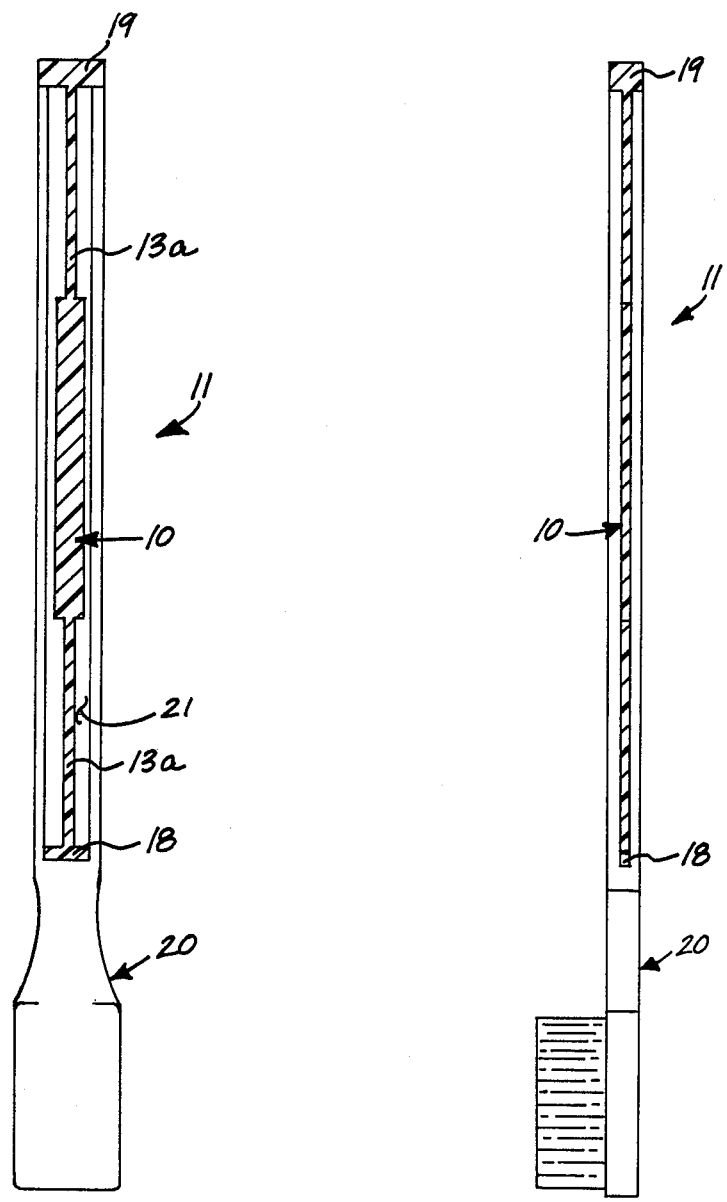

ORAL HYGIENE TOOL

BACKGROUND OF THE INVENTION

1. Field of the Invention

The present invention relates to that class of invention associated with oral hygiene instruments, and more specifically sets forth a toothbrush and associated tongue-scraping tool for removal of unwanted debris and tartar from a human tongue.

2. Description of the Prior Art

Oral hygienic tools are well known in the prior art and their use in maintaining desired oral care is well known. Tongue scraping has recently availed itself to massage and clean an associated tongue for improved circulation and removal of excess debris, including dead skin, bacteria, and tartar.

While flexible tools of various types have been known in the prior art, the use of providing a tongue-scraping tool, and particularly one in association within a toothbrush handle for providing a kit for the particular purpose of complete oral care, has not been presented in the prior art, as exemplified in U.S. design Pat. Nos. 32,481 to Berger setting forth a spatula device, as may be utilized in a cooking environment, 44,390 to Weder setting forth an applicator handle, 159,920 to Pablinetl setting forth an arcuately configured medicinal spoon, 161,947 to Margolis setting forth a peculiarly shaped pharmaceutical spoon, 215,775 to Jones setting forth an acne skimmer, and 249,802 to Lyman setting forth a tissue culture plate.

The aforenoted patents are of selection to illustrate various curvilinear planar-like tools for particular applications, but it may be appreciated that there is a need for a new and improved tongue scraper, and particularly a tongue scraper in combination with a toothbrush for presenting an oral hygiene kit for contemporary use, in a health conscious society.

SUMMARY OF THE INVENTION

In view of the foregoing disadvantages inherent in the known types of oral hygiene tools now present in the prior art, the present invention provides an oral hygiene tool and particularly an oral hygiene tool for use in combination with a toothbrush for presenting a compact toothbrush for conventional use and a tongue scraper for use in removing unwanted plaque and improving circulation on an associated tongue to be treated. As such, the general purpose of the present invention, which will be described subsequently in greater detail, is to provide a new and improved oral hygiene tool which has all the advantages of the prior art oral hygiene tools and none of the disadvantages.

To attain this, the present invention comprises a planar-like tool of generally arcuate configuration formed with a terminal, generally narrow handle, each formed with a first free end and a second end integrally formed to a wider tongue-scraping blade wherein the tool is of a flexible construction and formed of plastic-like or metallic flexible materials to enable accommodation of various tongue contours and insertion within a hollow handle of an associated toothbrush and may be further formed with extended tips at the aforenoted free ends for alignment within a cavity of the toothbrush and for enabling enhanced grasping of the tool when secured within the toothbrush.

My invention resides not in any one of these features per se, but rather in the particular combination of all of them herein disclosed and claimed and it is distinguished from the prior art in this particular combination of all of its structures for the functions specified.

There has thus been outline, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved oral hygiene tool which has all the advantages of the prior art oral hygiene tools and none of the disadvantages.

It is another object of the present invention to provide a new and improved oral hygiene tool which may be easily and efficiently manufactured and marketed.

It is a further object of the present invention to provide a new and improved oral hygiene tool which is of a durable and reliable construction.

An even further object of the present invention is to provide a new and improved oral hygiene tool which is susceptible of a low cost of manufacture with regard to both materials and labor, and which accordingly is then susceptible of low prices of sale to the consuming public, thereby making such oral hygiene tool economically available to the buying public.

Still yet another object of the present invention is to provide a new and improved oral hygiene tool which provides in the apparatuses and methods of the prior art some of the advantages thereof, while simultaneously overcoming some of the disadvantages normally associated therewith.

Still another object of the present invention is to provide a new and improved oral hygiene tool wherein a flexible tongue-scraping blade is formed of a material to enable accommodation of various tongue contours and formed with handles for grasping thereof and may be further positioned within the cavity of an associated toothbrush for storage when not in use to present an oral hygiene kit of convenient use and construction.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an orthographic side view of the tongue scraper of the instant invention.

FIG. 2 is a top orthographic view of the tongue scraper of the instant invention.

FIG. 3 is an orthographic view of the tongue scraper of the instant invention.

FIG. 4 is an orthographic bottom view of the oral hygiene kit of the instant invention.

FIG. 5 is a side orthographic view of the tongue-scraper kit of the instant invention.

DESCRIPTION OF THE PREFERRED EMBODIMENT

With reference now to the drawings, and in particular to FIGS. 1 to 5 thereof, a new and improved oral hygiene tool embodying the principles and concepts of the present invention and generally designated by the reference numeral 10 will be described.

More specifically, it will be noted that the oral hygiene tool 10 essentially comprises a central blade comprising a top surface 12, an equally spaced bottom surface 16, an parallel spaced sides 14 orthogonally formed to the top and bottom surfaces 12 and 16 respectively. The blade has secured thereto a plurality of handles each formed with a top surface 13 coextensive with the top surface of blade 12, bottom surfaces 16 coextensive with the bottom surface of the blade 16, and parallel even distantly spaced side surfaces 15 inwardly directed from the side surfaces 16 of the tongue-scraping blade. As illustrated in FIGS. 2 and 3, convex transitional surfaces 17 provide a smooth non-engaging transitional surface between the side surfaces 16.

It may be noted that the upper surface of the tool 10 is formed of a generally convex configuration with a spaced concave lower surface equally spaced from the top surface, as illustrated in FIG. 1 for example. The tool 10 is preferably formed of a plastic-like memory retentent material but may be formed of suitable aluminum or the like that maintains a flexible characteristic to accommodate various tongue surfaces to enable scraping of the blade 16 about the upper surface of a human tongue for the cleaning and massaging thereof.

In use, the oral hygiene tool 10 is merely grasped by the handles and pulled over an associated tongue to scrape and massage said tongue. FIGS. 4 and 5 illustrate an oral hygiene kit including the oral hygiene tool 10 and an associated toothbrush 20. The toothbrush 20 is formed with a cavity 21, as illustrated in FIG. 4, wherein the cavity is of a thickness of a complementary shape to that of the tool 10 to compactly store the same in a generally elongate configuration, as illustrated.

In this configuration, the oral hygiene tool 10 is formed with a first tip 18 of a width equal to that of the width of the cavity 21 and a second tip 19 greater than the width of the cavity 21 and equal to the toothbrush handle to prevent complete inclusion of the tool 10 and associated tip 19 with the cavity. A resultant grasping surface, as illustrated in FIGS. 4 and 5, by use of the second tip 19 is available to readily insert and withdraw the tool 10 relative to the cavity 21 of the toothbrush.

In this manner, the kit 11 enables a more complete oral hygiene procedure by a conventional brushing of teeth and subsequent tongue scraping, as noted above.

The manner of usage and operation of the instant invention should be apparent from the above description, and accordingly no further discussion relative to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An oral hygiene tool apparatus comprising, an elongate arcuate flexible strip of uniform thickness formed of memory retentent material, and said strip formed with a central blade of a first width positioned centrally of said arcuate flexible strip, and a handle of a plurality of handles integrally formed to said blade on each end of said blade, and each of said handle blending into said blade by means of a convex transitional surface to eliminate projections on said apparatus and minimize injury to a tongue when said apparatus is pulled over said tongue, and wherein said arcuate flexible strip is formed with a continuous convex upper surface and a continuous concave lower surface, and wherein each handle is of equal length, and wherein the uniform thickness of said strip is defined between said upper and lower surfaces, and wherein opposed parallel side surfaces of said blade and opposed parallel side surfaces of said handle and said surfaces of said blade are orthogonally oriented relative to said upper and lower surfaces, and wherein said side surfaces of said handle are of a lesser width than said side surfaces of said blade, and wherein said flexible strip is accommodated within a cavity of a toothbrush, said cavity is of a thickness equal to said thickness of said arcuate flexible strip, and wherein said strip further includes a first tip of a width greater than said width of said blade and said first tip is equal to said width of said cavity, and wherein said strip is formed with a second strip integrally secured to a distal terminal end of said strip opposed to said first tip wherein said second tip is of a width greater than said first tip and of a width equal to a width defined by said toothbrush to present a grasping surface externally positioned of said cavity.

* * * * *